United States Patent
Troetzschel et al.

(10) Patent No.: US 9,407,076 B2
(45) Date of Patent: Aug. 2, 2016

(54) ELECTRICAL BUSHING WITH GRADIENT CERMET

(71) Applicant: Heraeus Precious Metals GmbH & Co. KG, Hanau (DE)

(72) Inventors: Jens Troetzschel, Ronneburg-Neuwiedermus (DE); Goran Pavlovic, Schaafheim (DE); Harald Manhardt, Hanau (DE); Nicole Staudt, Friedberg (DE)

(73) Assignee: Heraeus Precious Metals GmbH & Co. KG, Hanau (DE)

( * ) Notice: Subject to any disclaimer, the term of this patent is extended or adjusted under 35 U.S.C. 154(b) by 394 days.

(21) Appl. No.: 14/023,096

(22) Filed: Sep. 10, 2013

(65) Prior Publication Data
US 2014/0008121 A1    Jan. 9, 2014

Related U.S. Application Data

(62) Division of application No. 13/018,882, filed on Feb. 1, 2011, now Pat. No. 8,528,201.

(30) Foreign Application Priority Data

Feb. 2, 2010 (DE) .......................... 10 2010 006 689

(51) Int. Cl.
*H02G 3/22* (2006.01)
*B29C 71/02* (2006.01)
(Continued)

(52) U.S. Cl.
CPC .. *H02G 3/22* (2013.01); *B28B 1/00* (2013.01); *B28B 11/24* (2013.01); *B29C 71/02* (2013.01);
(Continued)

(58) Field of Classification Search
CPC ..... A61N 1/05; A61N 1/3752; A61N 1/3754; H01R 13/5224; A61F 2/02; H04R 2225/67; H02G 3/22; H02G 1/00; H02G 3/18; B28B 1/00; B28B 11/24; B29C 71/02; Y10T 29/49117; Y10T 29/49158; Y10T 29/49163
USPC ............. 174/152 R, 659, 11 BH, 12 BH, 18, 174/152 GM, 257, 264, 262, 137, 138 R, 174/142; 607/37, 116, 117, 118, 119, 38, 5; 264/614; 361/302, 307, 306.1; 333/182; 439/909
See application file for complete search history.

(56) References Cited

U.S. PATENT DOCUMENTS

| | | |
|---|---|---|
| 4,352,951 A | 10/1982 | Kyle |
| 4,362,792 A | 12/1982 | Bowsky et al. |

(Continued)

FOREIGN PATENT DOCUMENTS

| | | |
|---|---|---|
| DE | 697 297 19 | 7/2005 |
| DE | 102009035971 | 2/2011 |
| DE | 102009035972 | 4/2011 |

OTHER PUBLICATIONS

Advisory Action for U.S. Appl. No. 12/850,412 mailed Apr. 14, 2014 (3 pgs.).

(Continued)

*Primary Examiner* — Angel R Estrada
(74) *Attorney, Agent, or Firm* — Dicke, Billig & Czaja, PLLC

(57) ABSTRACT

One aspect relates to a method for producing an electrical bushing for an implantable device, an electrical bushing, and an implantable device. The method according to one embodiment includes forming a base body from a ceramic slurry and introducing a bushing conductor made of a metal or cermet material with a metal fraction into the base body. The metal fraction in the bushing conductor is provided to decrease towards the base body. It includes sintering the green blank that includes the base body and the bushing conductor.

6 Claims, 3 Drawing Sheets

(51) Int. Cl.
  *B28B 1/00* (2006.01)
  *B28B 11/24* (2006.01)
  *H02G 3/18* (2006.01)
  *H02G 1/00* (2006.01)

(52) U.S. Cl.
  CPC . *H02G 1/00* (2013.01); *H02G 3/18* (2013.01); *Y10T 29/49117* (2015.01); *Y10T 29/49158* (2015.01); *Y10T 29/49163* (2015.01)

(56) References Cited

U.S. PATENT DOCUMENTS

| | | |
|---|---|---|
| 4,456,786 A | 6/1984 | Kyle |
| 4,488,673 A | 12/1984 | Hopper, Jr. |
| 4,678,868 A | 7/1987 | Kraska et al. |
| 4,737,601 A | 4/1988 | Gartzke |
| 4,774,953 A | 10/1988 | Foote |
| 4,816,621 A | 3/1989 | Huebner et al. |
| 4,991,582 A | 2/1991 | Byers et al. |
| 4,992,910 A | 2/1991 | Evans |
| 5,046,262 A | 9/1991 | Kerbaugh |
| 5,245,999 A | 9/1993 | Dahlberg et al. |
| 5,272,283 A | 12/1993 | Kuzma |
| 5,513,793 A | 5/1996 | Malmgren |
| 5,654,106 A | 8/1997 | Purnell et al. |
| 5,683,435 A | 11/1997 | Truex et al. |
| 5,738,270 A | 4/1998 | Malmgren |
| 5,750,926 A | 5/1998 | Schulman et al. |
| 5,769,874 A | 6/1998 | Dahlberg |
| 5,782,891 A | 7/1998 | Hassler et al. |
| 5,821,011 A | 10/1998 | Taylor et al. |
| 5,851,222 A | 12/1998 | Taylor et al. |
| 5,855,711 A | 1/1999 | Araki et al. |
| 5,861,714 A | 1/1999 | Wei et al. |
| 5,866,851 A | 2/1999 | Taylor et al. |
| 6,232,004 B1 | 5/2001 | Lasater |
| 6,284,080 B1 | 9/2001 | Haq et al. |
| 6,414,835 B1 | 7/2002 | Wolf et al. |
| 6,579,492 B2 | 6/2003 | Wehler |
| 6,586,675 B1 | 7/2003 | Bealka et al. |
| 6,660,116 B2 | 12/2003 | Wolf et al. |
| 7,068,491 B1 | 6/2006 | Burdon et al. |
| 7,107,099 B1 | 9/2006 | O'Phelan et al. |
| 7,222,419 B2 | 5/2007 | Horng et al. |
| 7,480,988 B2 | 1/2009 | Ok et al. |
| 7,569,452 B2 | 8/2009 | Fu et al. |
| 7,668,597 B2 | 2/2010 | Engmark et al. |
| 7,818,876 B2 | 10/2010 | Suaning |
| 7,901,761 B1 | 3/2011 | Jiang et al. |
| 7,930,032 B2 | 4/2011 | Teske et al. |
| 7,970,474 B2 | 6/2011 | Starke |
| 8,000,804 B1 | 8/2011 | Wessendorf et al. |
| 8,155,743 B2 | 4/2012 | Rundle et al. |
| 8,163,397 B2 | 4/2012 | Ok et al. |
| 8,189,333 B2 | 5/2012 | Foster |
| 8,494,635 B2 | 7/2013 | Troetzschel et al. |
| 8,528,201 B2 | 9/2013 | Troetzschel et al. |
| 8,886,320 B2 | 11/2014 | Troetzschel et al. |
| 8,929,987 B2 | 1/2015 | Troetzschel et al. |
| 9,048,608 B2 * | 6/2015 | Pavlovic ............ H01R 13/5224 |
| 9,088,093 B2 * | 7/2015 | Reisinger ........... H01R 13/5224 |
| 9,126,053 B2 * | 9/2015 | Kempf ................. A61N 1/3754 |
| 9,129,747 B2 * | 9/2015 | Pinwill ................. H01G 4/005 |
| 2001/0018012 A1 | 8/2001 | Harmand et al. |
| 2002/0166739 A1 | 11/2002 | Naerheim |
| 2003/0109903 A1 | 6/2003 | Berrang et al. |
| 2004/0023101 A1 | 2/2004 | Jacobson et al. |
| 2004/0128016 A1 | 7/2004 | Stewart |
| 2006/0025866 A1 | 2/2006 | Serafin, Jr. et al. |
| 2006/0247714 A1 | 11/2006 | Taylor et al. |
| 2007/0041164 A1 | 2/2007 | Greenberg et al. |
| 2007/0217121 A1 | 9/2007 | Fu et al. |
| 2007/0276389 A1 | 11/2007 | Franke et al. |
| 2008/0060834 A1 | 3/2008 | Eck et al. |
| 2009/0281586 A1 | 11/2009 | Lim |
| 2010/0121438 A1 | 5/2010 | Jarvik |
| 2011/0032658 A1 | 2/2011 | Iyer |
| 2011/0034965 A1 | 2/2011 | Troetzschel et al. |
| 2011/0034966 A1 | 2/2011 | Troetzschel et al. |
| 2011/0048770 A1 | 3/2011 | Reiterer et al. |
| 2011/0094768 A1 | 4/2011 | Davis et al. |
| 2011/0186349 A1 | 8/2011 | Troetzschel et al. |
| 2011/0190885 A1 | 8/2011 | Troetzschel et al. |
| 2011/0232961 A1 | 9/2011 | Teske |
| 2011/0232962 A1 | 9/2011 | Teske |
| 2013/0299233 A1 | 11/2013 | Troetzschel et al. |
| 2014/0008121 A1 | 1/2014 | Troetzschel et al. |
| 2014/0144014 A1 | 5/2014 | Troetzschel et al. |

OTHER PUBLICATIONS

Office Action for U.S. Appl. No. 12/850,412 mailed May 8, 2014 (11 pgs.).
Notice of Allowance for U.S. Appl. No. 12/850,412 mailed Sep. 2, 2014 (11 pgs.).
Restriction Requirement for U.S. Appl. No. 14/171,275 mailed Nov. 2, 2015 (6 pgs.).
Final Office Action for U.S. Appl. No. 13/942,685 mailed Apr. 14, 2014 (22 pgs.).
Notice of Allowance for U.S. Appl. No. 13/942,685 mailed Jul. 7, 2014 (5 pgs.).
Office Action for U.S. Appl. No. 12/850,406 mailed Sep. 17, 2012 (11 pages).
Final Office Action for U.S. Appl. No. 12/850,406 mailed Feb. 25, 2013 (16 pages).
Office Action for U.S. Appl. No. 12/850,406 mailed Sep. 12, 2013 (16 pages).
Dictionary definition of a cermet found at The Free Dictionary site http://www.thefreedictionary.com/cermets.
Notice of Allowance for U.S. Appl. No. 12/850,406 mailed Feb. 5, 2014 (9 pages).
Office Action for U.S. Appl. No. 12/850,412 mailed Sep. 17, 2012 (11 pages).
Final Office Action for U.S. Appl. No. 12/850,412 mailed Feb. 25, 2013 (18 pages).
Office Action for U.S. Appl. No. 12/850,412 mailed Sep. 11, 2013 (13 pages).
Final Office Action for U.S. Appl. No. 12/850,412 mailed Jan. 31, 2014 (8 pages).
Restriction Requirement for U.S. Appl. No. 13/018,882 mailed Dec. 20, 2012 (5 pages).
Notice of Allowance for U.S. Appl. No. 13/018,882 mailed May 10, 2013 (25 pages).
Notice of Allowability for U.S. Appl. No. 13/018,882 mailed Jul. 16, 2013 (6 pages).
Office Action for U.S. Appl. No. 13/018,847 mailed Dec. 5, 2012 (24 pages).
Notice of Allowance for U.S. Appl. No. 13/018,847 mailed Mar. 25, 2013 (25 pages).
Office Action for U.S. Appl. No. 13/942,685 mailed Dec. 23, 2013 (10 pages).

* cited by examiner

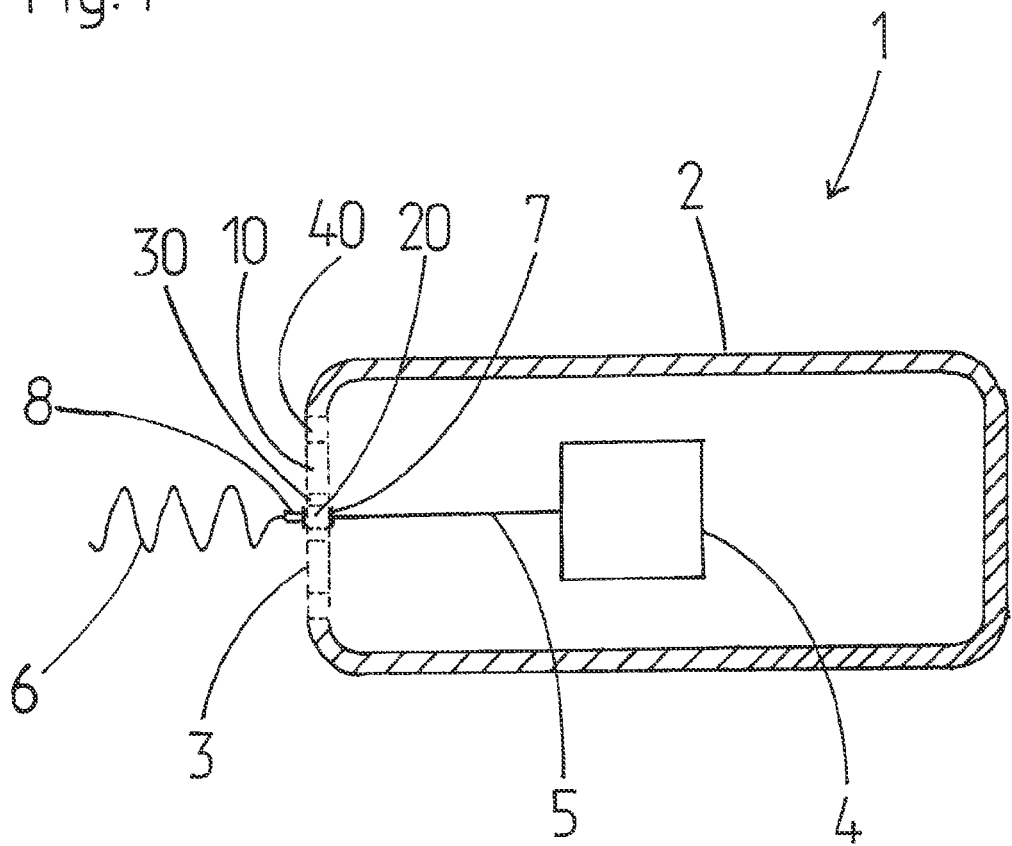

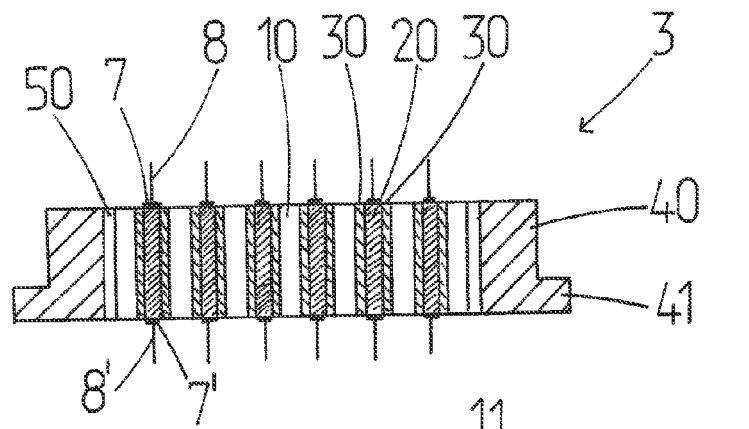
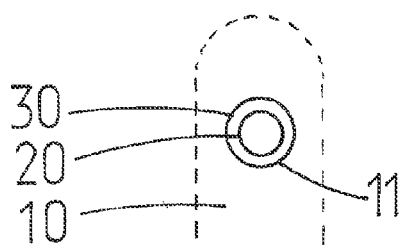
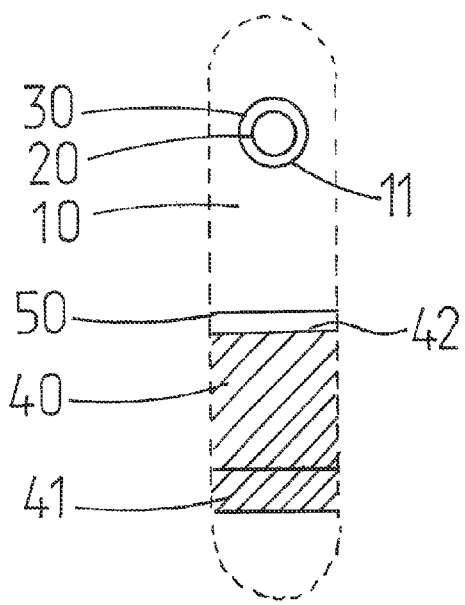

ELECTRICAL BUSHING WITH GRADIENT CERMET

CROSS-REFERENCE TO RELATED APPLICATIONS

This application is a divisional of U.S. patent application Ser. No. 13/018,882, entitled "METHOD OF PRODUCING AN ELECTRICAL BUSHING WITH GRADIENT CERMET," having a filing date of Feb. 1, 2011, which claims priority to German Patent Application No. DE 10 2010 006 689.3, filed on Feb. 2, 2010, all of which are incorporated herein by reference.

This Patent Application is also related to Utility patent application Ser. No. 13/018,847 filed on Feb. 1, 2011, entitled "METHOD FOR SINTERING ELECTRICAL BUSHINGS", which is incorporated herein by reference.

BACKGROUND

One aspect relates to a method for producing an electrical bushing for an implantable device, another to an implantable medical device, another to an electrical bushing as well as to an implantable device.

DE 697 29 719 T2 describes an electrical bushing for an implantable electrical therapeutic device. Electrical bushings of this type serve to establish electrical connection between a hermetically sealed interior and an exterior of the therapeutic device.

Known examples of implantable therapeutic devices include brain pacemakers, cardiac pacemakers or defibrillators. These devices commonly include a hermetically sealed metal housing which is provided with a connection body, also called header, on one side. The connection body includes a connection socket that serves for connection of electrode leads, which is effected, for example, by means of a bajonet lock. In this context, the connection socket includes electrical contacts that serve to electrically connect electrode leads to control electronics on the interior of the housing of the implantable device.

Hermetic sealing with respect to a surrounding is an essential prerequisite of a corresponding electrical bushing since the control electronics needs to be kept isolated from liquids in order to consistently prevent malfunctions or total failure. Since the conducting wires generally are metal wires or metal pins that are introduced into an electrically insulating ceramic base body of the electrical bushing, the interfaces between the conducting wires and the base body are weak spots. It needs to be ensured, therefore, that the signal-transmitting conducting wires that are introduced into the electrical bushing are introduced into the insulating element such as to be free of gaps.

A gap-free connection between the two elements is commonly generated by metallizing an internal surface of a bore hole in the base body and soldering to it a conducting wire that is guided through it. However, the application of the metallization in the bore hole in the insulating element is a difficult task. Homogeneous metallization of the internal surface of the bore hole in the insulating element are ensured only via cost-intensive procedures.

For these and other reasons there is a need for the present invention.

SUMMARY

One embodiment is a method for producing an electrical bushing for an implantable device characterized in that a green blank is produced from an electrically insulating base body and at least one electrically conductive bushing conductor that extends through the base body. It includes forming the base body from a ceramic slurry and introducing a bushing conductor made of a metal powder, metal slurry, cermet powder and/or cermet slurry into the base body. The metal fraction in the bushing conductor is provided to decrease towards the base body. It includes sintering the green blank that includes the base body and the bushing conductor.

BRIEF DESCRIPTION OF THE DRAWINGS

The accompanying drawings are included to provide a further understanding of embodiments and are incorporated in and constitute a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

The invention is described in the following, without limiting its general spirit, by means of exemplary embodiments making reference to the drawings, whereby we wish to explicitly refer to the drawings with regard to any and all details according to the invention that are not elaborated on in more detail in the description. In the figures:

FIG. 1 illustrates a schematic view of an implantable medical device.

FIG. 2 illustrates a schematic cross sectional view through an electrical bushing according to one embodiment.

FIG. 3 illustrates a schematic top view onto the electrical bushing according to the embodiment illustrated in FIG. 2.

FIG. 4 illustrates a magnified schematic view of a detail of the electrical bushing of FIG. 3.

DETAILED DESCRIPTION

Figure 5:
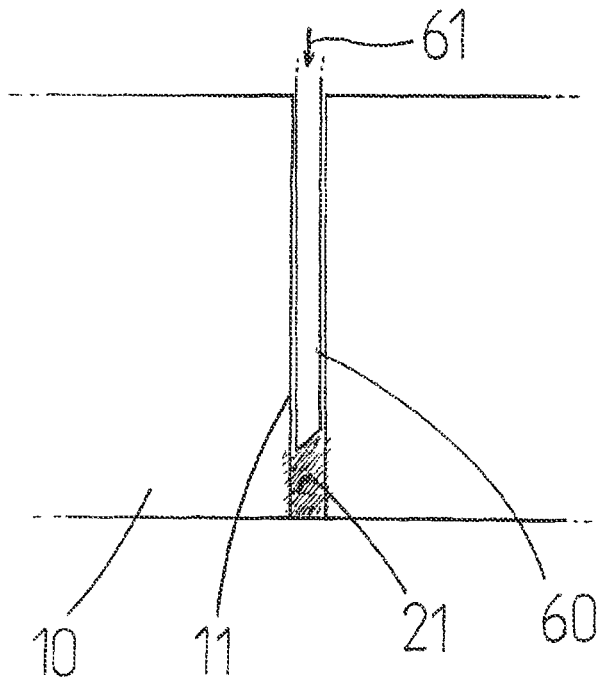
FIG. 5 illustrates a schematic depiction of a production method according to one embodiment.

In the following Detailed Description, reference is made to the accompanying drawings, which form a part hereof, and in which is shown by way of illustration specific embodiments in which the invention may be practiced. In this regard, directional terminology, such as "top," "bottom," "front," "back," "leading," "trailing," etc., is used with reference to the orientation of the Figure(s) being described. Because components of embodiments can be positioned in a number of different orientations, the directional terminology is used for purposes of illustration and is in no way limiting. It is to be understood that other embodiments may be utilized and structural or logical changes may be made without departing from the scope of the present invention. The following detailed description, therefore, is not to be taken in a limiting sense, and the scope of the present invention is defined by the appended claims.

It is to be understood that the features of the various exemplary embodiments described herein may be combined with each other, unless specifically noted otherwise.

In the figures below, identical or equivalent elements or corresponding parts are denoted with the same reference numbers such that no presentation thereof is provided again herein.

Based on the above-described prior art, one embodiment provides an electrical bushing for an implantable device, and in one embodiment, an implantable medical device, in which the above-mentioned disadvantages associated with the prior art are averted and the long-lasting hermetic sealing of the electrical bushing is ensured.

One embodiment is a method for producing an electrical bushing for an implantable device that is developed such that a green blank is produced from an electrically insulating base body and at least one electrically-conductive bushing conductor that extends through the base body, comprising the following steps:

forming the base body from a ceramic slurry;

introducing a bushing conductor made of a metal powder, metal slurry, cermet powder and/or cermet slurry into the base body, whereby the metal fraction in the bushing conductor is provided to decrease towards the base body;

sintering the green blank that comprises the base body and the bushing conductor.

In one embodiment, in place of the techniques used previously, in which an electrically conductive wire needed to be guided through a bushing made of a sintered ceramic material and soldered or welded to same, the bushing consists of a sintered material entirely and thus firmly bonded shaping throughout free of sites of fracture and hermetically sealing is attained. The problem that is encountered according to the prior art, being that the seam between a conducting wire and the surrounding sintered material of an insulating base body comes undone and thus breaks the hermetic sealing is thus prevented according to the embodiment, since a predetermined breakage site of this type is no longer present.

In the context of one embodiment, the term, "cermet", refers to a composite material made of ceramic materials in a metallic matrix. In its unprocessed state, it is a mixture of a ceramic powder and a metallic powder. Cermets are characterized by their particularly high hardness and resistance to wear. Cermets are materials that are related to hard metals, but dispense with the hard material, tungsten carbide, and are produced by powder metallurgical means. The sintering process for cermet proceeds alike the one for homogeneous powders. At identical compression force, the metal is compacted more strongly than the ceramic material. Compared to sintered hard metals, a cermet-containing positional element illustrates higher resistance to thermal shock and oxidation. The ceramic components of the cermet in most cases are aluminum oxide ($Al_2O_3$) and zirconium dioxide ($ZrO_2$), whereas niobium, molybdenum, titanium, cobalt, zirconium, and chromium are preferred in one embodiment as metallic components.

The material to be used according to one embodiment can be a dry powder that is compressed into a green blank in the dry state and possesses sufficient adhesion to maintain its compressed green blank shape. In the context of one embodiment, a slurry is a suspension of particles of a powder made of one or more material(s) in a liquid binding agent, commonly in water or in an organic binding agent. A slurry possesses high viscosity and is easy to shape into a green blank without having to apply high pressure.

In the case of green blanks made from slurries, the sintering process, which is generally carried out below the melting temperature of the ceramic, cermet or metal materials that are used, but in individual cases can also be carried out just above the melting temperature of the lower melting component of a multi-component mixture, this usually being the metal component, leads to the binding agent slowly diffusing from the slurry. Overly rapid heating leads a rapid increase of the volume of the binding agent by transition to the gas phase and destruction of the green blank or formation of undesired defects in the work-piece.

During sintering, sintering necks are formed between the particles of the green blank which effects firmly bonded connection of the particles to each other. Simultaneously, the particles of the material move closer together which reduces the size of hollow spaces between the particles until hermetic sealing of the sintered work-piece with respect to gases and liquids is attained. The work-piece shrinks during this process.

It is known that cermet-containing slurries, due to their metal fraction, are subject to more extensive shrinking during the sintering than pure ceramic slurries. Accordingly, there is a risk that the bushing body shrinks more strongly during the sintering than the pure ceramic base body such that no hermetic sealing of the two is established. This is solved according to one embodiment by means of the selection of the shapes of the openings and/or of the green blank bodies that are introduced into the openings as well as by application of a force.

The bushing conductor according to one embodiment in the base body consists of a sintered material, such as a sintered metal and/or cermet slurry or a metal and/or cermet powder, which is introduced into the base body first, before same is sintered in the form of an assembled green blank. In the process, a stepwise or gradually decreasing metal fraction, from the center of the bushing conductor to the base body surrounding the same, is established.

The metal fraction has a dual role. Firstly, the metal powder and/or the metal particles in the metal slurry and/or in the cermet become a continuous metallically and therefore electrically conductive conductor that enables a transmission of electrical current. Secondly, the metal in the cermet and/or in the metal powder also forms a matrix for ceramic particles embedded therein which are thus held therein and result in a particularly durable structure.

What the metal fraction decreasing from inside towards outside, also called gradient, effects is that the different shrinking behavior of a metal and/or cermet slurry or powder with respect to the surrounding ceramic slurry or ceramic powder is balanced out and tensions in the material occurring due to the different shrinkage are balanced out. The tensions are therefore not concentrated in one point and do not lead to defects in the material in said point.

An electrically conductive connection is established if the metal content of the cermet is in one embodiment 80% or more, and in another embodiment is 90% or more.

In a development of the method according to one embodiment, for introduction of the at least one bushing conductor into the base body, a bushing opening is generated in the base body and one or more organic films, such as in a concentric arrangement, which have a low combustion point and separate various volumes from each other, are introduced into the bushing opening, whereby metal powder, cermet powder, metal slurry and/or cermet slurry with different metal fractions are subsequently filled into the various volumes. In the context of one embodiment this means that the metal fraction of the material in one volume differs from that in another volume. In particular, materials with progressively decreasing metal fractions are filled in, progressing from inside towards outside, and thus a gradual gradient of the metal fraction of the material filled into the volumes is generated.

Separated by the organic films, the materials filled into the various volumes do not mix during the sintering. Since the organic films have a combustion temperature below the sintering temperature, they disintegrate during the sintering and diffuse from the green blank. Once the organic films have disintegrated, the adjoining materials of the initially separately filled volumes contact each other and form a firmly bonded sintered connection to each other.

In another embodiment, which can also be used in addition to the embodiment of the method discussed above, for introduction of the at least one bushing conductor into the base body, it is preferable to generate a bushing opening in the base body, form a bushing conductor green blank and insert it into the bushing opening of the base body. Green blanks of bushing conductors and bushing openings in the green blank of the base body can be shaped to a perfect fit and can be placed inside each other after removal from the mold. It is also feasible to introduce a corresponding green blank of a bushing conductor into an organic film according to the above-mentioned variant of the method or to initially wrap it with the film and then to introduce it into the bushing opening.

Prior to inserting it in the bushing opening, the bushing conductor green blank is enveloped in one or more transitional layers made of a cermet slurry whose metal fraction or metal fractions decrease(s) progressively from inside towards outside, in particular with respect to the metal fraction of the bushing conductor green blank. By this means, a gradient of the metal fraction of the bushing conductor from inside towards outside is established.

In another variant of the method according to one embodiment, which can also be used in addition to one or both of the embodiments of the method described above, for introduction of the at least one bushing conductor into the base body, the base body and/or a cermet slurry-filled volume of the bushing opening is punctured with an injection needle and the injection needle is retracted while injecting a metal powder, a metal slurry, a cermet powder and/or a cermet slurry.

In this variant, the material with the highest metal fraction is injected directly into the green blank of the base body or of a bushing conductor. When the injection needle punctures the material, it first generates a channel with the same diameter as the injection needle and the material that was situated in said space is pushed aside. Upon retraction of the injection needle, said channel is filled out with a material with a high metal fraction.

In one embodiment, the injection proceeds under pressure and the injected metal and/or cermet powder and/or the injected metal and/or cermet slurry penetrates into the surrounding material under pressure. Due to the penetration, the material with a high metal fraction mixes more strongly with the surrounding material with a low or non-existent metal fraction as compared to if it is filled-in without pressure such that a gradient and/or metal fraction that gradually decreases from inside towards outside is established in the material. Suitable injectors are known and work, for example, on the basis of piezo elements. Hydraulic or pneumatic pressure generators can also be used according to the embodiment.

The injection needle in one embodiment includes two or more injection channels in a concentric arrangement through which two or more materials with different metal fractions can be co-extruded or co-injected into the base body or into the bushing conductor. By this means, a bushing conductor or the core of a bushing conductor is generated in one procedural step that generates a metal fraction gradient that decreases from inside towards outside. In this context, according to one embodiment, the term, "extrude", refers to the injection of a metal or cermet slurry, whereas the term, "inject", refers to both a slurry and a powder.

If, after completing the sintering, at least one surface of the electrical bushing is polished and contacted with a metallic pin or wire in at least one place of the surface at which the at least one bushing conductor is arranged, a stable and hermetically sealed electrical bushing is attained. The contacting is effected by means of soldering or welding, whereby in particular laser welding and resistance welding lead to long-lasting contacting that conducts the electric current well. The contacting is effected by metallic wires or pins. Alternatively, the bushing conductor can be provided to be projecting beyond the electrical bushing and/or the base body and itself form a contacting pin. This means provides for current flow from one side of the bushing conductor to the other side.

A stable connection of an electrical bushing to a housing is achieved if, in addition, prior to the sintering, a wreath-shaped fringe body is formed from a cermet slurry and has a receiving opening for the base body into which the base body is inserted in order to form the green blank. Said green blank with the fringe body is then sintered, whereby the fringe body, having a metal fraction, enables good connection to a metallic housing of an implantable device.

One embodiment is an electrical bushing for an implantable device having an electrically insulating base body and at least one electrically conductive bushing conductor that extends through the base body, whereby the base body is produced from a sintered ceramic material, and which electrical bushing is developed such that the at least one bushing conductor consists of a metal and/or cermet material that has been jointly sintered with the base body and has a metal fraction that decreases from the interior of the bushing conductor towards the outside.

The corresponding electrical bushing according to one embodiment possesses the advantages mentioned above in relation to the method, for example in one embodiment, the firmly bonded production of the entire electrical bushing with a fully firmly bonded incorporation of the bushing conductor(s) in the insulating base body, whereby tension due to the different shrinking processes of the various metals during the sintering are reduced, in particular, by the metal fraction gradient from the bushing conduction to the material of the base body. This contributes to a long service life of the hermetic seal.

In one embodiment, the base body is connected circumferentially to a wreath-shaped fringe body made of a cermet material through a firmly bonded sintered connection, whereby the fringe body includes a receiving opening, in which the base body is arranged. Having the fringe body enables easy availability and/or ability of the electrical bushing to be connected in a housing of an implantable device.

In one embodiment, the electrical bushing is hermetically sealed for gases and liquids. For this purpose, for example, the sintering process is carried out until the material has compacted to the degree that no patent pores are present any longer.

An electrical bushing according to one embodiment can be or is produced according to any one of the methods according to the embodiments described above.

One embodiment is an implantable device having an electrical bushing of the type described above.

Features, advantages, and details specified in the context of one of the subject matters of one embodiment shall also apply to the respective other subject matters of other embodiments.

FIG. 1 illustrates a schematic view of an implantable medical device 1, for example a brain pacemaker, a cardiac pacemaker or a defibrillator. The device 1 includes a metallic and biocompatible housing 2 having an electrical bushing 3. An electronic measuring and control device 4 is arranged on the interior of the housing 2 and is connected to an electrically conductive bushing conductor 20 of the electrical bushing 3 by means of a connecting wire 5 and an electrical contact 7.

On the exterior of the bushing conductor 20, there is, beyond another electrical contact, a contact pin 8 to which a conducting coil 6, indicated schematically only, is attached that is connected to a stimulation electrode.

The electrical bushing 3 hermetically seals an opening in housing 2. In electrical bushing 3, the bushing conductor 20 is framed sequentially by transitional layers 30 and a base body 10, which includes on its circumference a fringe body 40 next to which the housing 2 is situated. The electrically insulating base body 10 prevents short-circuiting between the electrically conductive, extended conducting wire 5 and the metallic housing 2 and/or the fringe body 40 which is also partly metallic.

The base body 10 is made from an insulating composition of materials. Electrical signals proceeding through the conducting wire 5 are not to be attenuated or short-circuited by contacting the housing 2 of the implantable device 1. Moreover, the base body 10 must include a biocompatible composition to be suitable for medical implantation. For this reason, it is preferred in one embodiment for the base body 10 to consist of a glass-ceramic or glass-like material. Compositions of base body 10 materials that include at least one from the group, aluminum oxide ($Al_2O_3$), magnesium oxide (MgO), zirconium oxide ($ZrO_2$), aluminum titanate ($Al_2TiO_5$), and piezoceramic materials, are preferred in some embodiments. Said substances possess high electrical resistance and low dielectric losses. In addition, these properties are complemented by high thermal resistance and good biocompatibility. Biocompatible metals include, in some embodiments, metals from the group, titanium (Ti), tantalum (Ta), iridium (Ir), niobium (Nb), platinum (Pt) or an alloy including at least one of these metals.

The insulating composition of materials is a powder mass that illustrates at least minimal adhesion of the powder particles. This is commonly implemented in that a grain size of the powder particles does not exceed 0.5 mm. In this context, the green blank is produced either by compaction of powder masses or by shaping and subsequent drying. Green blanks of an insulating base body 10 and of electrically conductive bushing conductors 20 and, if applicable, of a fringe body 40 are produced in parallel, placed inside each other and fired subsequently.

FIG. 2 illustrates a schematic cross-section of an electrical bushing 3 according to one embodiment. The electrical bushing 3 includes a circumferential fringe body 40 that has been sintered from a cermet material and has a flange 41. Situated next to it towards the inside, there is a transitional layer 50 made of a cermet with a lower metal fraction than that of the fringe body 40, followed by a base body 10 made of a non-conductive, purely ceramic material.

Bushing conductors 20 are embedded in the base body 10 and jacketed each with a transitional layer 30. The transitional layer 30 consists of a cermet with a metal content of approx. 20% to approx. 70%, whereas the bushing conductor 20 includes a higher metal content and, in one embodiment, consists entirely of a sintered metallic material. Since the entire part illustrated in FIG. 2 is sintered, it represents a hermetic and stable electrical bushing 3.

The fringe body 40 includes a flange 41, whereby the flange, in one embodiment, is metallically conductive. The flange serves to seal the electrical bushing with respect to a housing 2 of the implantable device 1. The electrical bushing 3 is held in the implantable device 1 by the fringe body 40. The flange 41 forms a bearing that can be engaged by a lid of the implantable medical device 1, in a sealing manner. Accordingly, the fringe body 40 having the flange 41 can have a U- or H-shaped cross-section. Integrating at least one flange 41 into the fringe body 40 ensures secure, shock-resistant, and long-lasting integration of the electrical bushing 3 in the implantable device 1. In addition, the flange can be provided such that a lid of the implantable device 1 is connected to the fringe element 40 in a non-positive fit and/or positive fit manner.

FIG. 3 illustrates a schematic top view of the electrical bushing 3 according to one embodiment as illustrated in FIG. 2. Proceeding from outside to inside, the flange 41, the fringe body 40, a transitional layer 50, the base body 10, and, embedded therein, six bushing conductors that are arranged next to each and are each provided with a transitional layer 30 are illustrated. FIG. 3 also illustrates where a receiving opening 42 of the fringe body 40 for the base body 10, as well as a bushing opening 11 in the base body 10 for a bushing conductor 20, are situated.

FIG. 4 illustrates in more detail a detail of FIG. 3 that corresponds to the dashed lines and reference signs I from FIG. 3. Accordingly, FIG. 4 illustrates the layered structure of the electrical bushing 3. In this context, in one embodiment it is preferable to assemble the various bodies into a green blank and sinter them jointly.

FIG. 5 schematically illustrates a variant of the method according to one embodiment, in which an injection needle 60 is introduced into the electrically insulating base body 10. In the process, the injection needle 60 generates a bushing opening 11 whose internal diameter corresponds to the external diameter of the injection needle 60. Proceeding in an injection direction 61, a cermet material 21 having a high metal fraction or a purely metallic material that can be subjected to sintering is filled into the hollow space thus generated. This may proceed under pressure such that the cermet material 21, and therefore the metallic particles also, penetrate into the region surrounding the base body 10 by means of which a metal fraction gradient becomes established.

In FIG. 5, the injection needle 60 is illustrated already partly retracted from the bushing opening 11, whereby the hollow space thus generated has been filled up with a metal or cermet material 21 that can be subjected to sintering. The injection needle 60 is then pulled further from the channel thus generated, whereby the hollow space thus generated is filled out completely by the cermet material 21, which, if applicable, mixes with the surrounding material of the base body 10 by penetrating into it.

Figure 6:
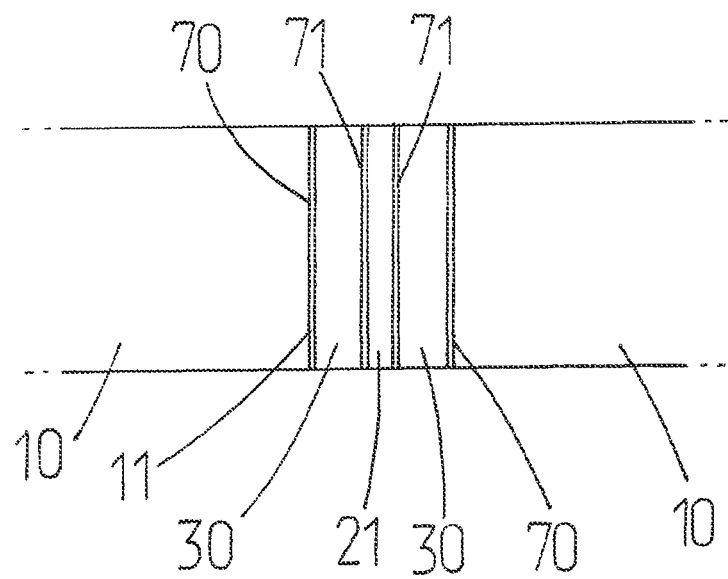
FIG. 6 illustrates a schematic depiction of another production method according to one embodiment.

FIG. 6 illustrates a schematic view of a step of an alternative variant of a method according to one embodiment. A bushing opening has been generated in the base body 10 first. A cermet material 21 and a transitional layer 30 have been introduced into the bushing opening 11 and are separated from each other and from the surrounding base body 10 by means of organic films 70, 71 in concentric arrangement such that they do not mix initially. The metal fraction of the cermet material 21, which may as well be a pure metal powder or a pure metal slurry, is higher than the metal fraction of the cermet material in the transitional layer 30.

The situation illustrated in FIG. 6 can be implemented by first generating a bushing opening 11 in the base body 10 and then lining the interior wall of said bushing opening 11 with an organic film 70. Subsequently, another organic film 71 is introduced into said hollow space such that two concentric cylindrical and/or ring-shaped volumes are separated from each other by means of said organic films 70 and 71. Subsequently, said volumes are filled with two different materials having different metal fractions.

Another method of implementing the situation according to FIG. 6 consists of first forming a green blank from the cermet material 21 followed by enveloping or wrapping the green blank with an organic film 71 before or after forming, then wrapping the organic film 71 with a material of a transitional layer 30, and, in turn, enveloping the latter with an organic film 70. This construct is then introduced into the bushing opening 11 generated earlier. Obviously, it is also feasible to combine components of the two production methods with each other and to apply a mixed form of the two variants described above.

In order to increase the electrical conductivity of the bushing conductor, it is also feasible to proceed according to FIG. 5 in the green blank in the place of the cermet material 21 on the interior of the organic film 71, and to penetrate into it with an injection needle and inject a pure metal powder or a pure metal slurry. This allows increments of metal fractions from inside towards outside of for example 100%, 90%, and 50% in the center, the immediately adjacent region, and the transitional area 30 to be implemented. A broad range of suitable metal fractions are available and need to be matched to the selected materials.

All specified features, including those evident from the drawings only, as well as individual features that are disclosed in combination with other features are considered essential for the embodiments both alone and in combination. Embodiments according to the invention can be provided through individual features or a combination of multiple features. Although specific embodiments have been illustrated and described herein, it will be appreciated by those of ordinary skill in the art that a variety of alternate and/or equivalent implementations may be substituted for the specific embodiments shown and described without departing from the scope of the present invention. This application is intended to cover any adaptations or variations of the specific embodiments discussed herein. Therefore, it is intended that this invention be limited only by the claims and the equivalents thereof.

What is claimed is:

1. An electrical bushing for an implantable device comprising:
   an electrically insulating base body; and
   at least one electrically conductive bushing conductor that extends through the base body;
   wherein the base body is produced from a sintered ceramic material, characterized in that the at least one bushing conductor comprises a metal or cermet material that has been jointly sintered with the base body and has a metal fraction that decreases from the interior of the bushing conductor towards the outside.

2. The electrical bushing according to claim 1, characterized in that the base body is connected circumferentially to a wreath-shaped fringe body made of a cermet material through a firmly bonded sintered connection, whereby the fringe body comprises a receiving opening, in which the base body is arranged.

3. The electrical bushing according to claim 1, characterized in that it is hermetically sealed for gases and liquids.

4. The electrical bushing of claim 1, which is produced by:
   forming the base body from a ceramic slurry;
   introducing the bushing conductor made of a metal powder, metal slurry, cermet powder and/or cermet slurry into the base body, whereby the metal fraction in the bushing conductor is provided to decrease towards the base body; and
   sintering the green blank that comprises the base body and the bushing conductor.

5. An implantable device comprising:
   an electrical bushing having an electrically insulating base body; and
   at least one electrically conductive bushing conductor that extends through the base body;
   wherein the base body is produced from a sintered ceramic material; and
   wherein the electrical bushing is characterized in that the at least one bushing conductor comprises a metal or cermet material that has been jointly sintered with the base body and has a metal fraction that decreases from the interior of the bushing conductor towards the outside.

6. The implantable device according to claim 5, characterized in that the electrical bushing is surrounded by transition layers comprising a cermet and a metal fraction that is lower than the metal fraction of the busing conductor.

* * * * *